United States Patent
Mazess

[19]

[11] Patent Number: 5,533,084
[45] Date of Patent: Jul. 2, 1996

[54] BONE DENSITOMETER WITH IMPROVED VERTEBRAL CHARACTERIZATION

[75] Inventor: Richard B. Mazess, Madison, Wis.

[73] Assignee: Lunar Corporation, Madison, Wis.

[21] Appl. No.: 344,255

[22] Filed: Nov. 23, 1994

Related U.S. Application Data

[63] Continuation-in-part of Ser. No. 241,270, May 10, 1994, which is a continuation-in-part of Ser. No. 67,651, May 26, 1993, Pat. No. 5,291,537, which is a division of Ser. No. 944,626, Sep. 14, 1992, Pat. No. 5,228,068, and a continuation-in-part of Ser. No. 73,264, Jun. 7, 1992, Pat. No. 5,306,306, which is a continuation of Ser. No. 862,096, Apr. 2, 1992, abandoned, which is a continuation of Ser. No. 655,011, Feb. 13, 1991, abandoned.

[51] Int. Cl.[6] .................................................. G01B 15/02
[52] U.S. Cl. .................. 378/54; 378/55; 378/56
[58] Field of Search ................... 378/51, 53, 54, 378/55, 56, 58, 62, 98, 146

[56] References Cited

U.S. PATENT DOCUMENTS

| | | | |
|---|---|---|---|
| 4,721,112 | 1/1988 | Hirano et al. | 378/54 X |
| 4,811,373 | 3/1989 | Stein | 378/54 |
| 5,172,695 | 12/1992 | Cann | 378/54 X |
| 5,228,068 | 7/1993 | Mazess | 378/54 |
| 5,235,628 | 8/1993 | Kalender | 378/56 X |
| 5,291,537 | 3/1994 | Mazess | 378/54 |
| 5,306,306 | 4/1994 | Bisek et al. | 623/16 |

OTHER PUBLICATIONS

Lunar Corporation, Operator's Manual for DPX, DPX-L, DPX-αlpha, and DPX-A Software, Sep. 1992.

*Primary Examiner*—David P. Porta
*Attorney, Agent, or Firm*—Quarles & Brady

[57] ABSTRACT

A dual energy densitometer includes a solid statement near x-ray detector which may be swept across the patient with movement of both to produce a matrix of data elements representing attenuation through the patient. Each of these data elements may be characterized as to its material type by the use of the data element values, templates representing general rules to be applied to the bone and operator input. The operator input is provided by a cursor controlled paintbrush which changes classifications of individual pixels based on a selected brush type.

12 Claims, 5 Drawing Sheets

BONE DENSITOMETER WITH IMPROVED VERTEBRAL CHARACTERIZATION

FIELD OF THE INVENTION

This is a continuation-in-part of application Ser. No. 08/241,270 filed May 10, 1994 based on a PCT filing of Sep. 10, 1993 which is a continuation-in-part of Ser. No. 08/067,651 filed May 26, 1993 U.S. Pat. No. 5,261,587, which is a divisional of Ser. No. 944,626, U.S. Pat. No. 5,228,068 filed Sep. 14, 1992; and a continuation-in-part of application Ser. No. 08/073,264 filed Jun. 7, 1992, U.S. Pat. No. 5,306,306, which is a continuation of application Ser. No. 07/862,096 filed Apr. 2, 1992, now abandoned, which is a continuation of application Ser. No. 07/655,011 filed Feb. 13, 1991, now abandoned.

The present invention relates to bone densitometers and in particular, to densitometers which analyze x-ray attenuation data to distinguish between bone and other materials in the body to identify particular bones and measure those bones.

BACKGROUND OF THE INVENTION

Digital bone densitometry devices such as the DPX machines manufactured by LUNAR Corporation of Madison, Wis. or the QDR machines manufactured by Hologic, Inc. of Waltham, Mass., are used to generate broadly based values of bone character, such as bone mineral content ("BMC") or bone mineral density ("BMD"). Such information about bone character, and in particular, about bone character in the spine is often relied on to diagnose and treat bone depletive disorders such as osteoporosis.

Traditionally, BMC and BMD measurements have been made by scanning the spine of a patient with a radiation source directed along an anterior-posterior ("AP") axis. One problem with AP scans of the spine for BMC and BMD measurement is that the measurement of the diagnostically significant trabecular bone in each vertebra is biased by contribution from the posterior elements of each vertebra. This is because bone from the posterior elements overlays much of the vertebral body in an AP view and projects into the intervertebral space. Thus most of the bone of the posterior elements were invariably included in the AP spine measurement.

To avoid these problems, manufacturers have resorted to measuring the spine from the lateral position. In the lateral position, it is argued, the region of interest can be easily limited to the vertebral body excluding the posterior elements. Thus, one avoided having the measurement biased by the posterior elements.

Nevertheless, significant problems exist with the lateral view. Because patient thickness is greater in the lateral view, imaging is compromised. For the same signal to noise ratio as is obtained in the AP view, in the lateral view one must increase the flux of the x-ray beam several fold which leads to an increased dose. If flux was not increased, the ability to define the margins of the vertebral body was no better and in many instances was worse than with the AP view.. Further, most of the lateral view of the spine is obstructed by the ribs or the pelvis. It can be appreciated by those skilled in the art, that such an obstruction presents a similar biasing problem as discussed above with respect to the posterior elements in the AP view.

At best, only two vertebrae, L3 and L4, present an unobstructed lateral view and this is true only for 20 percent of the population. In the small percentage of the population where an unobstructed view is possible, if the vertebrae have a pathology, such as crush fractures, the BMC or BMD measurement of those vertebrae may not be clinically relevant.

SUMMARY OF THE INVENTION

The present invention improves the measurement of bone BMC or BMD in the AP direction by defining a measurement region of interest (ROI) about a vertebra that avoids areas of the vertebra that are significantly biased by the superposition of the spinal posterior elements. A digital computer analyzes both the attenuation values of acquired data elements and the location of those data elements to identify high density areas likely caused by the posterior elements. These areas are eliminated from the measurement ROI.

Specifically, the vertebrae are scanned with a beam of radiation directed in the AP direction to acquire a matrix of discrete data elements each having a value and a defined location through the vertebra. A digital computer reviews the values of the data elements and their defined locations to identify individual vertebra and zones of data elements within the individual vertebra where the data elements measure radiation substantially attenuated by the bone of both the centrum and the spinal processes;

These zones may be located by identifying an intervertebral space adjacent to the vertebra body and data elements within the intervertebral space measuring radiation substantially only attenuated by spinal process and not by centrum to produce a reference measurement. The reference measurement may be subtracted from a peak value of the data elements in the vertebrae to establish a limit with those data elements within the vertebrae having a value greater than the limit defining the zones.

The zones are then excluded from a calculation of the physical characteristic of the material of the vertebra, which is displayed.

Thus, it is one object of the invention to provide a measurement of bone density in the AP direction that avoids the biasing effects of the spinal processes.

This technique can be similarly applied to locating and eliminating the intervertebral spaces from the measurement of vertebral density. Here the values of data in the region of the intervertebral space and the location of that data in conjunction with the known structure of the spine are used to accurately locate intervertebral spaces and to eliminate these spaces from the density measurement.

Specifically, the data elements of the vertebrae, acquired as described above, are sorted based on their values into bone data elements measuring the physical characteristic of the vertebrae. The defined locations of these bone elements are used to identify the spinal column and the intervertebral spaces, and a bone integrity value for the vertebrae is determined, which excludes the intervertebral spaces.

Thus, it is another object of the invention to eliminate not only the effects of denser posterior elements from the vertebral measurement but also the influence of less dense regions of the intervertebral spaces.

A highly flexible and interactive method for selecting what data elements will be included in the measurement is provided by the use of "paintbrush" cursor which allows the operator to selectively change the characterization of data elements by "painting" their corresponding pixels on an image of the data elements.

Specifically, a two dimensional array of pixels having values representing the attenuation of radiation at locations through the patient are displayed on a digital computer having a display screen and a cursor controller providing a select signal and cursor coordinates in response to operator commands. The digital computer receives the array of pixels and categorizes the pixels into at least bone pixels, soft tissue pixels and neutral pixels. An image of the pixels is displayed in which at least one category is visually distinguishable from the others. In response to cursor coordinates from the cursor controller a cursor symbol is moved in a path on the image. Pixels in the path have their categorization changed when the select signal is received. A diagnostic value is displayed to the operator based on the bone pixels and soft tissue pixels but excluding the neutral pixels, as each is affected by the operator under cursor control.

Thus, it is another object of the invention to permit the operator to fine tune the characterization of each data element in an interactive manner.

Other objects, advantages, and features of the present invention will become apparent from the following specification when taken in conjunction with the accompanying drawings.

DESCRIPTION OF THE PREFERRED EMBODIMENT DENSITOMETRY HARDWARE

Figure 1:
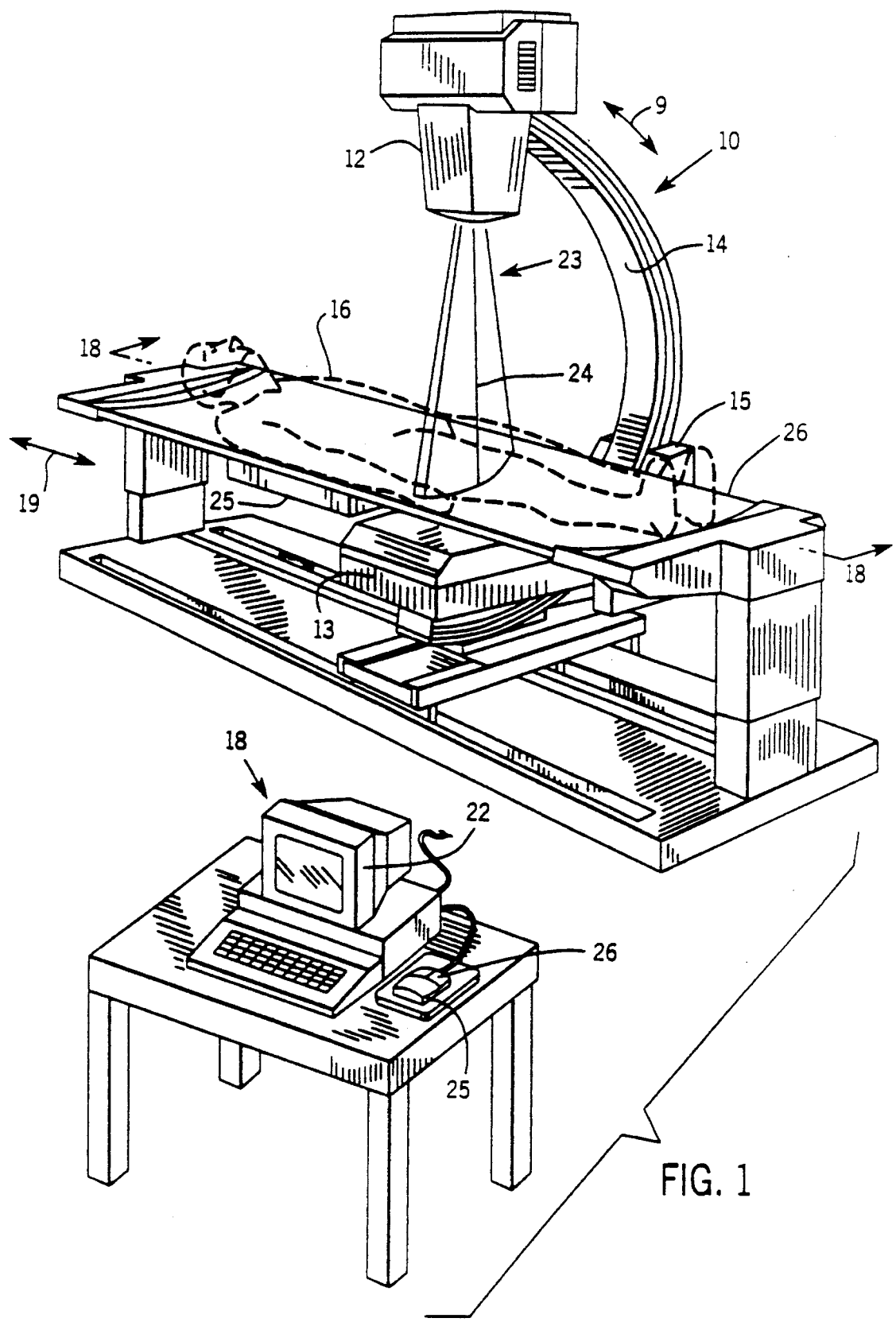
FIG. 1 is a perspective view of an instrument for use in the present invention showing a C-arm supporting at one end an x-ray source producing a fan beam whose plane is aligned with a supine patient's transverse plane and received by a linear detector at the other end of the C-arm, the C-arm to be scanned along an inferior/superior axis of the patient to produce a matrix of data elements that may be displayed on a computer.

Shown in FIG. 1 is a perspective view of a dual energy bone densitometer of the type employed in the preferred embodiment of the present invention.

The densitometer 10 includes a radiation source 12 and a detector 13, both of which are mounted on a rotatable C-arm 14, which extends on either side of a supine patient 16 so as to direct and receive radiation along a radiation axis 24 through the patient 16.

The C-arm 14 is designed to be rotated in a vertical plane as indicated by arrows 9 as supported by a collar 15 so as to allow both an AP view of the spine or other bones or a lateral view of the same. In the present invention, however, rotation of the C-arm is not required and a fixed arm positioned for AP imaging may be used.

The C-arm 14 may also be moved longitudinally along the patient's body in a scanning direction 19 and may be positioned under the control of servo motors under computer control as is understood in the art.

The densitometer 10 of the preferred embodiment employs a dual energy x-ray source. "Dual energy x-ray" or "polychromatic x-ray" refers to radiation at two or more bands of energy, emitted simultaneously or in rapid succession, or a single broad band energy of more than a few keV over the diagnostic imaging range. The dual energy x-ray beam is used for the measurements of bone character (i.e. BMC and BMD).

The radiation source 12 may provide a fan beam 23 of x-rays which is collimated and oriented toward the vertebra such that the plane of the fan beam 23 is perpendicular to the longitudinal axis of the spine. The orientation of the fan beam 23 perpendicular to the spine allows imaging of the spine, or other long bones generally aligned with the spine such as the femur, with minimal distortion along the longitudinal axis resulting in the ability to measure vertebral dimensions in this axis with greater accuracy than possible with a cone beam. For greater accuracy in the horizontal axis, the fan beam 23 may also be oriented so that the vertebral body or other bone is irradiated by the center portion of the beam rather than the edges which are subject to distortion. Since the center of a fan beam 23 has little angulation, the resulting data is comparable to that obtained with a pencil beam and yet a scan can be obtained much faster.

The detector 13 is a linear array of detector elements subtending the fan beam 23 for providing simultaneous measurements along a number of rays of the fan beam 23 associated with each such detector element.

A general-purpose digital computer 18, is programmed for use in operating the densitometer 10 and analyzing the data obtained from the detector and includes specialized algorithms for carrying out the calculations required by the present invention. In addition, the present invention includes a data acquisition system ("DAS") for converting the signals produced by the detector 13 to a form compatible with the computer 18 and a data storage device (neither of which are shown) which may be incorporated in the computer 18.

The computer 18 provides an electronic display 22 for outputting the data analysis or images of the data as will be described. A "mouse" 25 or other cursor control device is provided to permit the operator to control a cursor (not shown in FIG. 1) on the display 22 in response to movement of the mouse 25 over a surface by the operator. Control buttons 26 on the mouse allow for additional operator input associated with the selection of menu items and modifying images on the display 22 as will be described in more detail below.

In most general terms, during operation of the densitometer 10, the radiation source 12 emits radiation of a certain energy level or levels along the radiation axis 24 at defined locations along the scan. The radiation passes through the vertebra 20 being scanned and is then received by the detector 13. The analog output of the detector 13 is sampled and digitized so as to produce a signal consisting of discrete data elements, each associated with a location through the patient, by the DAS. The DAS may then transmit the digitized signal to the computer 18 which stores the data in computer memory (not shown) or on a mass storage device.

When the fan beam 23 is poly-energetic, discrimination between high and low energy attenuation of x-rays by the patient can be done by the detector 13. Two sets of side by side detector elements may be used, one each selectively sensitive to high energies or to low energies. Thus, during the scan the detector 13 produces data for high and low energy image. These two images may later be aligned and mathematically combined to produce bone density information according to mathematical algorithms known in the art. Alternatively the detector 13 can be a stacked array. In this arrangement, high and low energy detector elements are stacked the low energy detector on top of the high energy detector. A particular advantage of the stacked array detector is that it can easily accommodate a multilinear array or area detector design. Such stacked detectors are described and claimed in Barnes, U.S. Pat. Nos. 4,626,688 and 5,138,167, incorporated herein by reference.

Figure 2:
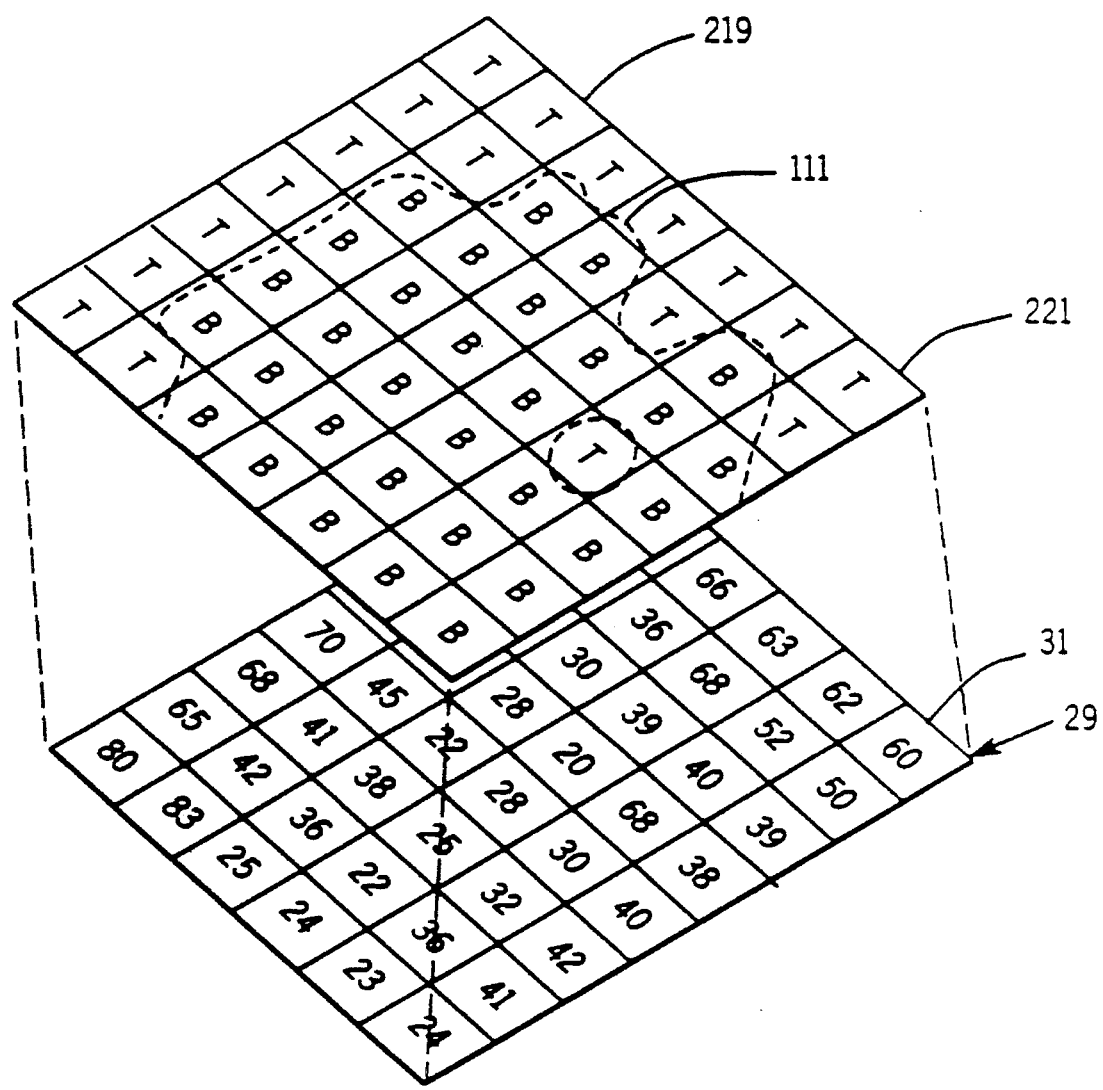
FIG. 2 is a schematic representation of the matrix of data elements produced by the instrument of FIG. 1 showing a point typing of each data element as bone or soft tissue.

Referring now to FIGS. 1 and 2, upon completion of the scanning of the patient 16 by the radiation source 12 and detector 13 the computer 18 arranges the data elements obtained in the scan in a matrix 29 within computer memory. Each data element 31 of the matrix is associated with a spatial location defined by the position of the C-arm 14 when the data element 31 is acquired during the scan and indicated in the matrix by the position of the data element 31 in the matrix. The spatial separation of the defined locations of the data elements 31 is determined by the distance that the instrument, e.g., the radiation source 12 and detector 13, moves between acquiring rows of data elements 31 and by the separation of detector elements in the detector 13.

Each data element 31 has a relative value proportional to the amount of radiation transmitted by the tissue at the corresponding location. The absorption of radiation by a tissue correlates to certain physical properties of that tissue. For example, bone absorbs a greater amount of radiation than does soft tissue. The data elements 31 thus obtained are referred to PBM for pseudo bone mineral content. The numbers are pseudo values because they are non-calibrated and therefore dimensionless. At this point in the analysis, therefore only the relative differences between the data elements 31 are significant, not their absolute values. While the calibration for each data element 31 could be done at this point, it is consumptive of computer resources, and thus is deferred and the PBM values are used.

PROCESSING OF DENSITOMETRY DATA

Figure 9:
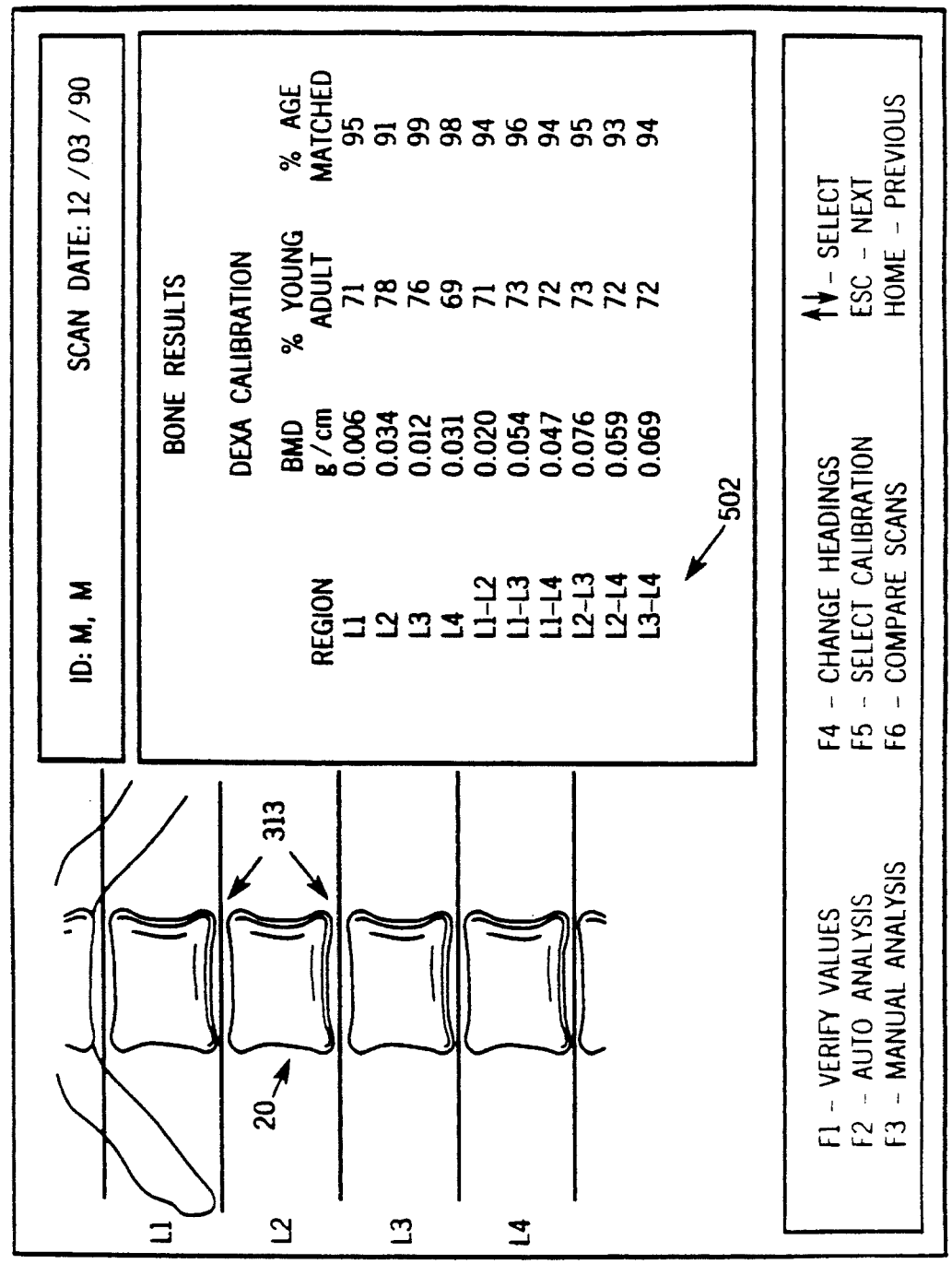
FIG. 9 is a representation of a prior art display of the computer similar to that of FIG. 6 showing definition of regions of interest that the intervertebral spaces and reward spinal processes as superimposed over the image of the vertebral body.

Referring momentarily to FIG. 9, prior art densitometers produced relatively low resolution images 500. For this reason, it is difficult with prior art bone densitometers for the operator to resolve the superior and inferior margins of the vertebral body 20 and exclude the areas of the intervertebral space 313. For similar reasons the lateral margins of the vertebrae 20 are also difficult to resolve. Thus, manufacturers and user of such devices establish large regions of interest 502 which include several vertebrae 20, typically L1–L4, or L2–L4 and the lateral margins are determined using arbitrary threshold designed to exclude the transverse processes, but not to conform to the true outline of the vertebral body. Placement and shape of the ROI is approximate. Because several vertebrae are measured, the intervertebral space is included in the measurement.

Figures 3, 4:
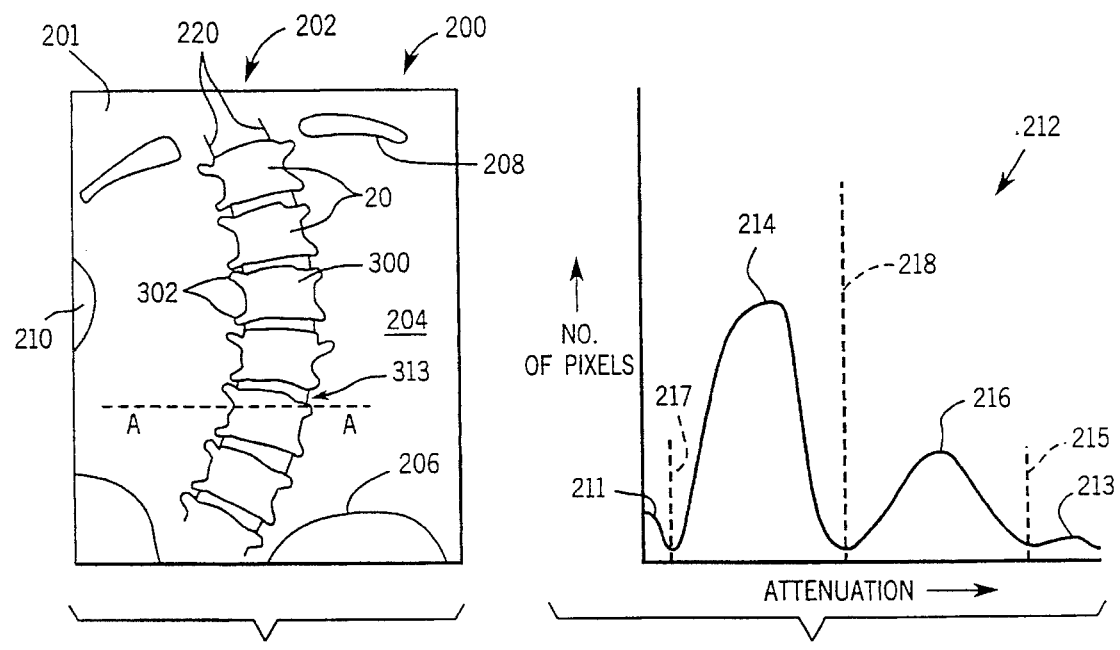
FIG. 3 is a greatly simplified representation of an image of a matrix of data elements acquired by the instrument of FIG. 1 showing representative vertebrae of the spine as well as portions of the clavicle and ilium where each data element is represented as a pixel on the image.
FIG. 4 is a histogram plotting the frequency of occurrence of the pixels in the image of FIG. 3 against the value of their corresponding data element showing distribution of the pixels into two modes corresponding to bone pixels and soft tissue pixels.

Referring now to FIG. 3, the data elements collected during the scan may be displayed as an image 200 where the spatial location of each data element 31 in the patient maps to a pixel 201 having a corresponding spatial location in the image 200; and where the value of each data element is interpreted as a shade of gray and/or a color of that pixel 201. Data elements recording the greatest attenuation of x-ray radiation are given the lightest gray values in the image 200 so that image 200 looks like a conventional x-ray radiograph with areas of bone, having the greatest attenuation, depicted generally as white and areas of lesser attenuation such as soft tissue and air depicted generally as black.

The typical image 200 will show the spine 202 resolving of the various vertebrae 20 surrounded by soft tissue 204 and by portions of other bones of the body such as the ilium 206 and clavicle 208. The resolution of the densitometer 10 must be such as to clearly delineate the margins of the vertebra. In some images 200, the x-ray fan beam 23 will pass outside of the patient's body altogether and the image 200 will include areas of air 210.

When dual energy is used, this initial image 200 may be created by combining the high and low data values of each location to produce an effective polyenergetic image.

Referring to FIGS. 3 and 4, the values of the data elements will be generally spread through the range of attenuation values. Further, within those data elements measuring only bone or only soft tissue will also vary over a range of values. Accurate computer analysis of this data requires that each data element and hence each pixel 201 in the image 200 be identified as to its tissue type. This identification or "point typing" is required not only to properly calibrate the algorithms used in employing the dual energy measurements (which need reference measurements of tissue types) but also to permit automated measurement of the vertebra by the computer.

Figure 5:
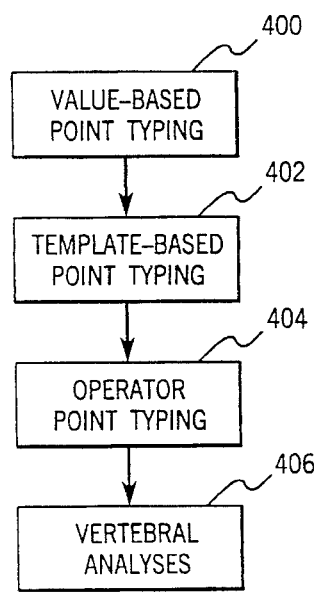
FIG. 5 is a flow chart depicting the steps of refining the point typing of the data elements of FIG. 2 into multiple of categories based on their value, their spatial distribution, and operator commands.

Referring now also to FIG. 5, a first step of point typing is performed by examining the values of the data elements 21 of each pixel 201 in the image 200 as indicated by process block 400. In this value-based point typing, each pixel 201 of the image 200 is sorted according to a plurality of attenuation ranges forming the horizontal axis of an effective attenuation histogram 212. The vertical axis of the histogram 212 indicates the number of pixels 201 of image 200 that have a particular attenuation value. As shown in FIG. 4, typically the pixels 201 will exhibit a bi-modal distribution with a first soft tissue mode 214 and a second bone mode 216.

The histogram shown in FIG. 4 reflects the fact that there is a range of pixel values and in particular pixel values that fall between the modes 214 and 216. A threshold 218 having a particular attenuation value must therefore be identified between these modes 214 and 216, for example, at the minima of the histogram 212 between the peaks or maxima of the modes 214 and 216. This threshold 218 is used to categorize each of the pixels 201 of the image 200 as either bone or soft tissue based on its value.

In images 200 which include pixels associated with data elements 31 that measure only air or that measure a metallic implant, additional modes 211 and 213, respectively, will be present outside of the modes 214 and 216 and low and high attenuations, respectively. These modes 211 and 213 can be used to generate additional thresholds 217 dividing the air pixels of mode 211 from the soft tissue pixels of mode 214, and threshold 215 dividing the artifact pixels of mode 213 from the bone pixels of mode 216.

Referring now to FIG. 2, each data element corresponding to the pixels 201 of image 200 may be compared to the thresholds 217, 218, and 215 to assign them a point type 219 on type matrix 221 in addition to its value. Thus, pixels 201 having attenuation values greater than the threshold 218 (but below threshold value 215) are assigned to bone category "B", whereas pixels 201 having a value less than the threshold 218 (but greater than threshold 217) are assigned a tissue value "T". A border 111 between bone elements "B" and tissue elements "T" may thus be established and used for further analyses of the bone, per process block 406 to be described, such as the making of morphometric measurements of a particular vertebra such as described in U.S. Pat. Nos. 5,228,068 and 5,291,537 assigned to the assignee of the present application and hereby incorporated by reference.

Often this value-based point typing is alone insufficient. This is particularly true where it may be desired to measure only a certain type of bone, as may be the case when one is measuring bone loss in individuals. For example, it is believed that the vertebral body of the vertebra, (the centrum) having a large proportion of trabecular bone is a more sensitive indicator of bone loss than the harder and denser cortical bone found, for example, in the spinal processes. For this reason, it may be desired to exclude, as much as possible, the denser spinal processes which arguably dilute the measurement of change in bone density, remaining relatively constant even as trabecular bone is lost.

Value-based point typing may also be insufficient because of measurement errors (from noise or quantization) and variations caused by intervening tissue. For this reason, referring to process block 402 of FIGS. 3 and 5, the value-based point typing is augmented by a template-based point typing. In template-based point typing, knowledge about the shape of a typical spinal vertebra is used to refine the point typing. Generally, template-based point typing applies rules about bone shape specific to the bone being investigated. For example, with the spine 202, it is known that the vertebrae 20 generally are aligned with each other along a slowly varying spinal axis and that their width is relatively constant. This "template" is used to fit two boundary lines 220 to the left and right boundaries of the spine 202 based on the value-based point typing previously performed at process block 400. The boundary lines 220 are fit to the bone pixels use of well known curve fitting algorithms which provide the best fit of a curve described by a polynomial equation of given order points so identified.

Generally, the points to which the curve is fit may be identified examining the point typing of the type matrix 221 across horizontal lines in the image 200 to identify the boundary pixels 201 at which the soft tissue "T" gives way to a bone "B".

Selecting the appropriate low order curve, based on knowledge of the anatomy of a general spine, allows the spinal processes 302 projecting laterally from the vertebra in the AP projection to be excluded from the bone measurement. In this template-based point typing, the bone outside of the boundary lines 220 is given a neutral characterization which means that it is neither classified as bone nor soft tissue but is excluded from the calculation of bone values.

A similar template fitting may be used to accurately identify the intervertebral spaces 313. Here, vertical paths through the type matrix 221 are taken and the inferior and superior borders of the vertebra 20 identified by the points at which the bone characterization "B" gives way to the tissue characterization "T" and vice versa. Low order curves fit to these points and perpendicular to the boundary lines 220 accurately establish intervertebral spaces 313 which if included in a bone density calculation might bias density calculations. Although the intervertebral spaces are generally not empty of pixels having a bone classification, in part due to the projection of the rearward spinal prosthesis through the intervertebral spaces, the curve fitting process may be adjusted to ignore these inclusions of bone to provide sharp intervertebral boundaries.

Thus, with value-based point typing 400 and template-based point typing 402, a more robust characterization of each point into the categories of bone or soft tissue is made.

Figure 7:
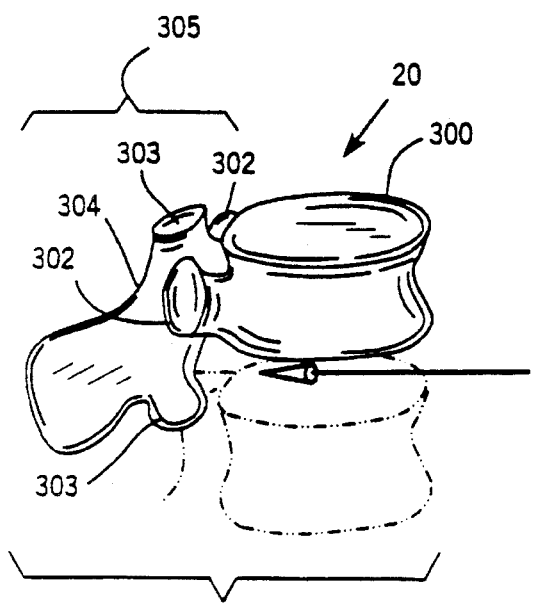
FIG. 7 is a perspective view of a vertebra showing the centrum and rearward extending spinal prosthesis.
Figure 8:
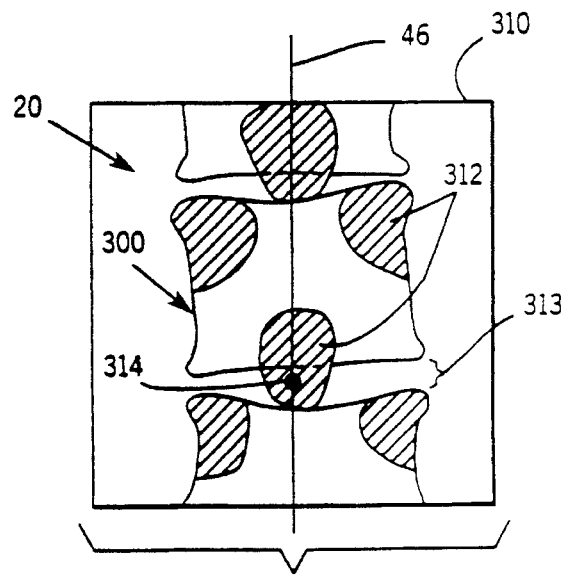
FIG. 8 is a simplified representation of an AP bone density image such as shown in FIG. 3 showing zones of high density caused by the superposition of the rearward spinal prosthesis on the centrum and the identification of a reference area in the intervertebral space used for removing these high density zones from the ultimate density measurement.

Referring now to FIGS. 7 and 8, the information from the values of the data elements 31 and their locations may be further used to identify points of high bone density such as represent a superposition of the spinal processes over the vertebra image. As shown in FIG. 7 vertebra 20 includes a generally cylindrical centrum 300 which bears most of the load of the body and which includes a high percentage of trabecular bone. As noted above, trabecular bone has been determined to be a sensitive indicator of bone change in the early stages of osteoporosis. Ideally then, bone density measurements of the spine would primarily measure trabecular bone.

Extending in the posterior direction from the centrum 300 are transverse processes 302, the inferior and superior articular processes 303, and the spinal lamina 306. Henceforth, for simplicity, these posterior structures will be collectively termed spinal processes 305. The bone of the spinal processes 305 is of higher density than the centrum 300 and include little trabecular bone.

Referring now to FIG. 8, in an AP bone density image 310, the spinal processes 305 (not directly visible) form zones of higher density 312 superimposed on the image of the centrum 300. These zones 312, when averaged into the vertebral average bone density reading for the vertebra 20 bias the average density upward possibly obscuring clinically significant loss in the trabecular bone mass. For this reason, it is desirable to identify and eliminate these zones 312 from the measurement process.

While it is possible to locate these zones 312 with respect to the landmarks on the vertebra 20 alone, as projected in the image 310, variations in vertebra 20 make it preferable that these zones be distinguished by establishing certain threshold levels of bone density indicative of the zones 312. That is, if the density of a data element 31 of the image 310 is above the established threshold, it is assumed that this data element 31 measures, in significant part, the bone of the spinal processes 305.

The particular density threshold, defining zones 312, will vary depending on the patient. Accordingly, the threshold is determined by a reference density measurement made at an established position with respect to the vertebrae 20. This procedure is performed by the computer 18 operating on the matrix 29 of data elements 31 as has previously been described.

Referring momentarily also to FIG. 3, the left and right spinal boundary lines 220 are used to identify the approximate horizontal center of the intervertebral spaces 313. The superior and inferior borders of adjacent vertebra 20, previously detected, are used to determine a vertical center of the intervertebral space 313. A vertical and horizontal vertebral center 314 is thus determined.

A cluster of data elements 31 around this center 314 is averaged to determine a density value of the spinal processes 305 without the intervention of the centrum 300. This value will be used as a reference measurement to identify the zones 312.

Each data element 31 within the vertebra 20 is next identified by the point typing previously described and the identification of the boundary lines 220 and the intervertebral spaces. Those data elements 31 are analyzed to find the data element 31 indicating maximum bone density or peak value within the vertebra 20. The previously determined reference value is then subtracted from the peak value to provide a density limit identifying the zones 312.

Now only data elements 31 within the vertebra 20 having density values beneath this limit are used in the calculation of the vertebral average bone density for the vertebra 20 thus effectively excluding zones 312 from the analysis of vertebral average bone density. Data elements 31 having higher values are considered to be upwardly biased by the spinal processes 305 and are ignored. The vertebral average bone density is thus the sum of the data elements 31 within the vertebrae 20 excluding zones 312 divided by the area encompassed by those included data elements 31. This density is an area density, e.g. grams per $cm^2$.

Referring again to FIG. 5, the value-based point typing 400 and the template-based point typing 402 are desirably augmented by operator point typing 404 in which the operator interactively changes the categories of certain pixels 201. This operator point typing enlists the superior knowledge of a trained operator in identifying bone and soft tissue in the context of a radiographic-like image of the bone and soft tissue. The operator point typing also permits use of the system to image and measure bones for which templates incorporating general knowledge about the bone anatomy have not been developed. This may occur for other bones in the body (e.g., hands or feet) or for individuals whose bones do not conform to the generalized rules stored within the equipment. Such flexibility may also be desired if the equipment is to be used with animal studies.

Important to the operator point typing is the provision of a suitable interface between the operator and the computer to facilitate the operator's recharacterization of the particular pixels 201. Such an interface should, to the extent possible, prevent inadvertent changing of data elements by the operator. The present invention realizes these goals by adopting a "paintbrush" interface in which the operator maneuvers a cursor "paintbrush" over the image to change the point typing of selected data elements.

Figure 6:
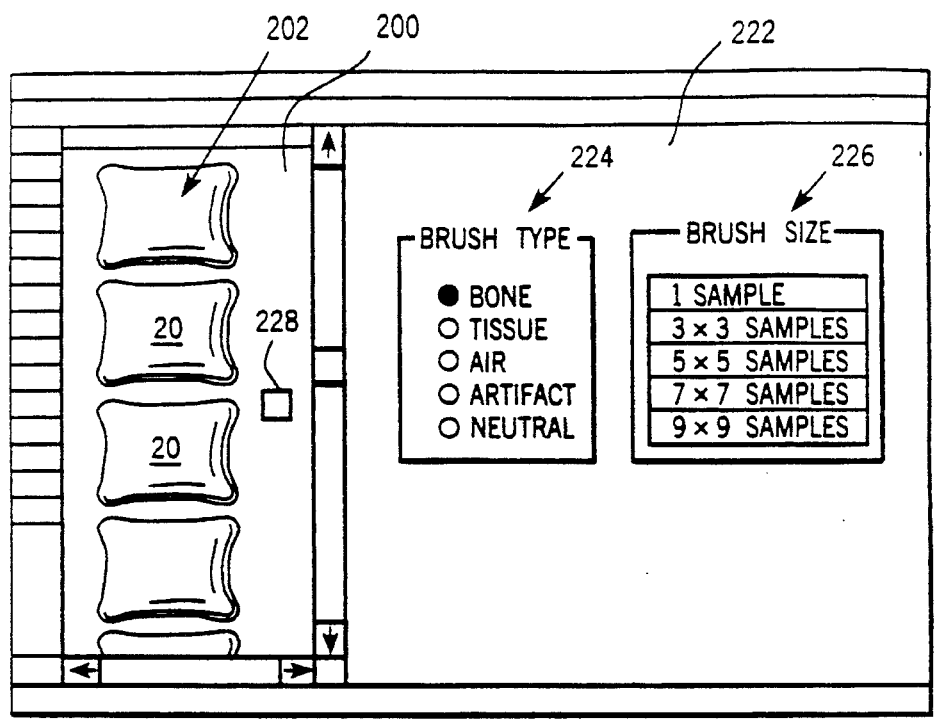
FIG. 6 is a representation of the display of the computer of FIG. 1 showing operator menus for selecting a brush type and brush size used by the operator for changing the point typing associated with the image of FIG. 3.

Referring now to FIG. 6, the image 200 is displayed to the operator on the display 22 together with a menu screen 222 having a brush type menu 224 and a brush size menu 226. Such menu systems are well known in the computer art and provide graphically for the input of operator parameters. In particular, the brush type menu 224 offers five different brushes: bone, tissue, air, artifact and neutral. When a particular brush type is selected, the material of the selected brush type is highlighted in the image 200 with a blue color according to the current point typing. Thus, when bone is selected as the brush type as indicated in Fig. 6, those pixels 201 previously identified by the point typing of processes 400 and 402 will be highlighted in blue. All materials, including bone, also take a gray scale value based on the values of their data elements 31 as has been described. Thus, all the data of the scan is available to the human operator in making determinations of point type.

If the tissue brush type is selected, the tissue pixels 201 will be highlighted in blue and the bone tissues will revert solely to black and white gray values. The categories of air and artifact in the present example would highlight no tissue as no pixels 201 have been characterized as either air or artifacts. The neutral characterization will highlight the portions of the ilium 206, the clavicle 208 and the processes 302 previously excluded by the value-based and template-based point typing of process box 400 and 402.

Pixels 201 are selected by the operator by use of a "paintbrush" cursor 228 whose position may be controlled by the mouse 25 as previously described with respect to FIG. 1 or other well known cursor controlled devices. As the mouse 25 is moved, the image of the cursor 228 moves on the image 200 providing an interactive real time control of point-typing of points by the operator.

After the operator moves the cursor 228 to a particular point on the image 200, the mouse button 26 may be depressed causing those data elements corresponding to the region of the image 200 covered by the cursor 228 to be changed to the characterization indicated by the brush type menu 224. Preferably, the mouse is used dynamically in the manner of a paintbrush with the button 26 continuously depressed wherein the swept area of the cursor 228 as it is moved over the image 200 in a path defines those pixels 201 changed to the new classification.

For example, if the bone brush type is being used, pixels 201 selected by the operator will be changed into the bone classification.

The brush size may be changed from one sample, that is, one pixel of the image through square shapes up to 9×9 samples or pixels 201. Thus, for rapid removal of extraneous bone into the neutral classification, a large paintbrush may be used, whereas a small paintbrush may be used for correction of individual point classifications, for example, between the intervertebral spaces.

The paintbrush allows flexible adjustment of the ROI to conform exactly to the vertebral body.

For measurements of bone density, this operator adjustment of classification can significantly enhance the clinical value of the measurement with minimum risk of affecting its reproducibility. Although changing pixels 201 classified as bone into, for example, neutral has the effect of eliminating those pixels 201 from the calculation of bone density, it also eliminates those pixels 201 from the divisor used in the density calculation. Thus, for a homogenous bone recharacterization of some of its pixels 201 as neutral, for example, will not affect the overall density measurement. On the other hand, the use of the cursor 228 to remove the denser regions of the spinal processes 302 even at the expense of removing some bone which is substantially trabecular only can substantially increase the sensitivity of the density measurement in the detection of loss of bone mass.

Referring again to FIG. 5, once the point typing is complete the total bone content for the bone pixels identified to a vertebra 20 may be determined per process block 406 and printed out on the display 22. Total bone content is the above computed vertebral average bone density (converted to a per data element 31 value) times the total number of data elements 31 within the vertebrae regardless of whether they are in zones 312 or not.

The combination of the intervertebral boundaries and the left and right boundary lines 220 may be used to accurately define a vertebral region to be used for calculating bone density for that particular vertebra 20.

In addition, bone density measurements may be made at particular regions for entire vertebrae or collections of vertebrae within the spine 202. Prior to these density measurements, the point typing may be used to calibrate a dual energy algorithm based on a soft tissue reading so as to remove the effects of intervening soft tissue superimposed over the bones of interest.

It is thus envisioned that the present invention is subject to many modifications which will become apparent to those of ordinary skill in the art. Accordingly, it is intended that the present invention not be limited to the particular embodiment illustrated herein, but embraces all such modified forms thereof as come within the scope of the following claims.

I claim:

1. A method of measuring bone density of vertebrae of a spine, the vertebrae including centrums of trabecular bone with rearward extending denser spinal processes, the method comprising the steps of:
   (a) scanning the vertebrae with a beam of radiation directed along an anterior-posterior axis to acquire a matrix of discrete data elements each having a value and a defined location through said vertebrae, and wherein the value of each data element is related to a physical characteristic of the material of the vertebrae at the defined location;
   (b) employing a digital computer to:
      (1) review the values of the data elements and their defined locations to identify at least one vertebra;
      (2) identify zones of data elements within the at least one vertebra where the data elements measure radiation substantially attenuated by the bone of both the centrum and the spinal processes;
      (3) exclude the zones identified in step (b)(2) from a calculation of the physical characteristic of the material of the at least one vertebra; and
   (c) display the measure of the physical characteristic determined in step (3).

2. The method of claim 1 wherein the physical characteristic is bone density.

3. The method of claim 1 wherein the physical characteristic is bone content.

4. The method of claim 1 wherein step (2) comprises:
   (i) using the locations of the vertebra identified in step (b)(1) to locate an intervertebral space adjacent to the vertebra;
   (ii) identifying data elements in the intervertebral space measuring radiation substantially only attenuated by spinal process and not by the centrum to produce a reference measurement;
   (iii) employing the reference measurement to identify data elements within the vertebrae having significant attenuation by spinal processes; and
   (iv) identifying the zones by the data elements identified in step (iii).

5. The method of claim 4 wherein step (iii) further comprises:
   subtracting the value of the reference measurement from a peak value of the data elements in the vertebrae to establish a limit; and
   identifying all data elements within the vertebrae having a value greater than the limit as the data elements within the vertebrae having significant attenuation by spinal processes.

6. The method of claim 1 wherein the radiation is dual energy x-ray radiation and the values of the matrix of discrete data elements are dual energy measurements of bone density.

7. The method of claim 1 wherein the displayed measure of bone density is expressed as a mass of bone per an identified vertebra.

8. A method of measuring bone density of vertebrae of a spine in a body, the vertebrae separated by intervertebral spaces to form a spinal column, the method comprising the steps of:
   (a) scanning the body with a beam of radiation directed in the anterior-posterior direction to acquire a matrix of discrete data elements each having a value wherein each said data element corresponds to a defined location in the body, and wherein the value of each data element is related to a physical characteristic of the material through which the beam of radiation passes;
   (b) employing a digital computer to:
      (1) sort the data elements based on their values into bone data elements measuring the physical characteristic of the vertebrae;
      (2) fit a template based on a general spine to the bone data elements and their defined locations to identify the spinal column and the intervertebral spaces;
      (3) determine a bone integrity value-based on the values of the bone data elements within the spinal column excluding the identified intervertebral spaces; and
   (c) display the bone integrity value determined in step (3).

9. The method of claim 8 wherein the physical characteristic is bone density.

10. The method of claim 8 wherein the physical characteristic is total bone content.

11. The method of claim 8 wherein step b(2) comprises:
   (i) using the locations of the bone data elements identified in step (b)(1) to locate a right and left spinal boundary;
   (ii) analyzing the locations and values of the bone data elements within the left and right spinal boundary to locate the intervertebral spaces.

12. The method of claim 8 wherein the radiation is dual energy x-ray radiation and the values of the matrix of discrete data elements are dual energy measurements of bone density.

* * * * *